United States Patent
Lee et al.

(10) Patent No.: US 11,307,646 B2
(45) Date of Patent: Apr. 19, 2022

(54) METHOD AND APPARATUS FOR ACQUIRING INFORMATION BY CAPTURING EYE

(71) Applicant: Samsung Electronics Co., Ltd., Suwon-si (KR)

(72) Inventors: Dong-Hi Lee, Suwon-si (KR); Ki-Huk Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 16/346,486

(22) PCT Filed: Nov. 3, 2017

(86) PCT No.: PCT/KR2017/012436
§ 371 (c)(1),
(2) Date: Apr. 30, 2019

(87) PCT Pub. No.: WO2018/084649
PCT Pub. Date: May 11, 2018

(65) Prior Publication Data
US 2020/0050257 A1 Feb. 13, 2020

(30) Foreign Application Priority Data
Nov. 4, 2016 (KR) .................. 10-2016-0146959

(51) Int. Cl.
*A61B 3/14* (2006.01)
*G06F 3/01* (2006.01)
(Continued)

(52) U.S. Cl.
CPC .............. *G06F 3/011* (2013.01); *A61B 3/14* (2013.01); *G02B 27/0172* (2013.01);
(Continued)

(58) Field of Classification Search
CPC ........ G06F 3/011; G06F 1/163; G06F 3/0488; A61B 3/14; G02B 27/0172; G06K 9/00597
(Continued)

(56) References Cited

U.S. PATENT DOCUMENTS 5,963,300 A * 10/1999 Horwitz ................. A61B 3/112
351/209
6,634,749 B1 10/2003 Morrison et al.
(Continued)

FOREIGN PATENT DOCUMENTS

CN 102540464 A 7/2012
CN 105975083 * 9/2016 ............... G09G 5/38
(Continued)

OTHER PUBLICATIONS

CN 105975083 Google Translation (Year: 2016).*
(Continued)

*Primary Examiner* — Nguyen T Truong

(57) ABSTRACT

The present invention relates to a method and an apparatus for acquiring information by capturing an eye or an area around an eye. A wearable electronic device according to various embodiments of the present invention may comprise: a light source; at least one lens; an optical surface disposed on a first side of the at least one lens; and a camera for receiving, through the at least one lens and the optical surface, light output from the light source and scattered by a subject located on a second side of the at least one lens.

17 Claims, 11 Drawing Sheets

(51) Int. Cl.
  *G02B 27/01* (2006.01)
  *G06F 1/16* (2006.01)
  *G06F 3/0488* (2022.01)
  *G06K 9/00* (2022.01)

(52) U.S. Cl.
  CPC ............ *G06F 1/163* (2013.01); *G06F 3/0488* (2013.01); *G06K 9/00597* (2013.01); *G02B 2027/0138* (2013.01)

(58) Field of Classification Search
  USPC .......................................................... 348/78
  See application file for complete search history.

(56) References Cited

U.S. PATENT DOCUMENTS

| | | |
|---|---|---|
| 2012/0127284 A1 | 5/2012 | Bar-Zeev et al. |
| 2015/0103152 A1* | 4/2015 | Qin ........................ G02B 13/08 348/53 |
| 2015/0198811 A1 | 7/2015 | Hoellwarth |
| 2015/0253573 A1 | 9/2015 | Sako et al. |
| 2015/0378162 A1 | 12/2015 | Bailey et al. |
| 2016/0062121 A1 | 3/2016 | Border et al. |
| 2016/0370591 A1 | 12/2016 | Wilson et al. |

FOREIGN PATENT DOCUMENTS

| | | |
|---|---|---|
| JP | 2002529763 A | 9/2002 |
| KR | 10-2004-0027764 A | 4/2004 |
| KR | 10-0949743 B1 | 3/2010 |
| KR | 10-2015-0056521 A | 5/2015 |
| WO | 2013/138647 A1 | 9/2013 |
| WO | 2016/103525 A1 | 6/2016 |

OTHER PUBLICATIONS

Supplementary European Search Report dated Sep. 10, 2019 in connection with European Patent Application No. 17 86 6683, 7 pages.
ISA/KR, "International Search Report and Written Opinion of the International Searching Authority," International Application No. PCT/KR2017/012436, dated Jan. 22, 2018, 12 pages.
Yirka, Bob, "Study shows men better at reading emotions in other men than in women," Medical Xpress, Apr. 15, 2013, 2 pages. http://medicalxpress.com/news/2013-04-men-emotions-women.html.
Zhang, Yu, "Region-Based Face Morphing Under Anthropometric Control," Jan. 15, 2019, 8 pages. http://zhangyu.50megs.com/AnthropometricControl.htm.
National Intellectual Property Administration, PRC, "The First Office Action", dated Mar. 3, 2021, in connection with Chinese Patent Application No. 201780068143.8, 18 pages.

* cited by examiner

METHOD AND APPARATUS FOR ACQUIRING INFORMATION BY CAPTURING EYE

CROSS-REFERENCE TO RELATED APPLICATIONS

This application is a National Phase Entry of PCT International Application No. PCT/KR2017/012436, which was filed on Nov. 3, 2017, and claims priority to Korean Patent Application No. 10-2016-0146959, which was filed on Nov. 4, 2016, the contents of which are incorporated herein by reference.

BACKGROUND

1. Field

The present disclosure relates to a method and apparatus for obtaining information by capturing an eye.

2. Description of the Related Art

Recently, portable electronic devices have changed into forms wearable on human bodies (or wearable devices). For example, portable electronic devices have been provided in various forms which are attachable to or detachable from a body or clothing, such as a head-mounted type (e.g., a head-mounted display or head-mounted glasses), a wrist-worn type (e.g., a watch or a wristband), a contact lens type, a ring type, a shoe type, a clothing type, etc. As an electronic device is provided as a wearable device, a user of the electronic device may avoid the inconvenience of carrying the electronic device.

In recent years, many head-mounted type electronic devices (hereinafter, collectively referred to as head-mounted displays (HMDs)) have been released. Examples of the HMDs may include see-through type HMDs which provide augmented reality (AR) and see-closed type HMDs which provide virtual reality (VR).

SUMMARY

Meanwhile, the HMD is worn on a user's body part (e.g., a user's head) to provide an AR or VR environment to the user, such that a way to receive an input from the user is limited. In particular, the user having worn the HMD has trouble using fingerprint authentication or iris authentication.

Various embodiments disclosed herein provide a method and an apparatus to solve the foregoing and other problems. According to an embodiment of the present disclosure, a user having worn an HMD may perform iris recognition without having to putting off the HMD.

A wearable electronic device according to various embodiments of the present disclosure includes a light source, at least one lens, an optical surface positioned on a first side of the at least one lens, and a camera configured to receive light, which is output from the light source and scattered by a subject located on a second side of the at least one lens, through the at least one lens and the optical surface.

A method of obtaining information by capturing an eye according to various embodiments of the present disclosure includes identifying an image corresponding to light received by a camera, by using a wearable electronic device including a light source, at least one lens, an optical surface positioned on a first side of the at least one lens, and the camera configured to receive light, which is output from the light source and scattered by a subject located on a second side of the at least one lens, through the at least one lens and the optical surface, and controlling at least one of the light source, the at least one lens, the optical surface, and the camera, based on the identified image.

According to various embodiments disclosed herein, a method and an apparatus may be provided in which a user may perform iris recognition without having to putting off an HMD. Moreover, by scanning an eye of the user having worn the HMD and a surrounding area of the eye and displaying a virtual image corresponding to a scanning result through a display provided in the HMD, senses of immersion of the user of the HMD and another person communicating with the user of the HMD may be improved.

DETAILED DESCRIPTION

Figure 1:
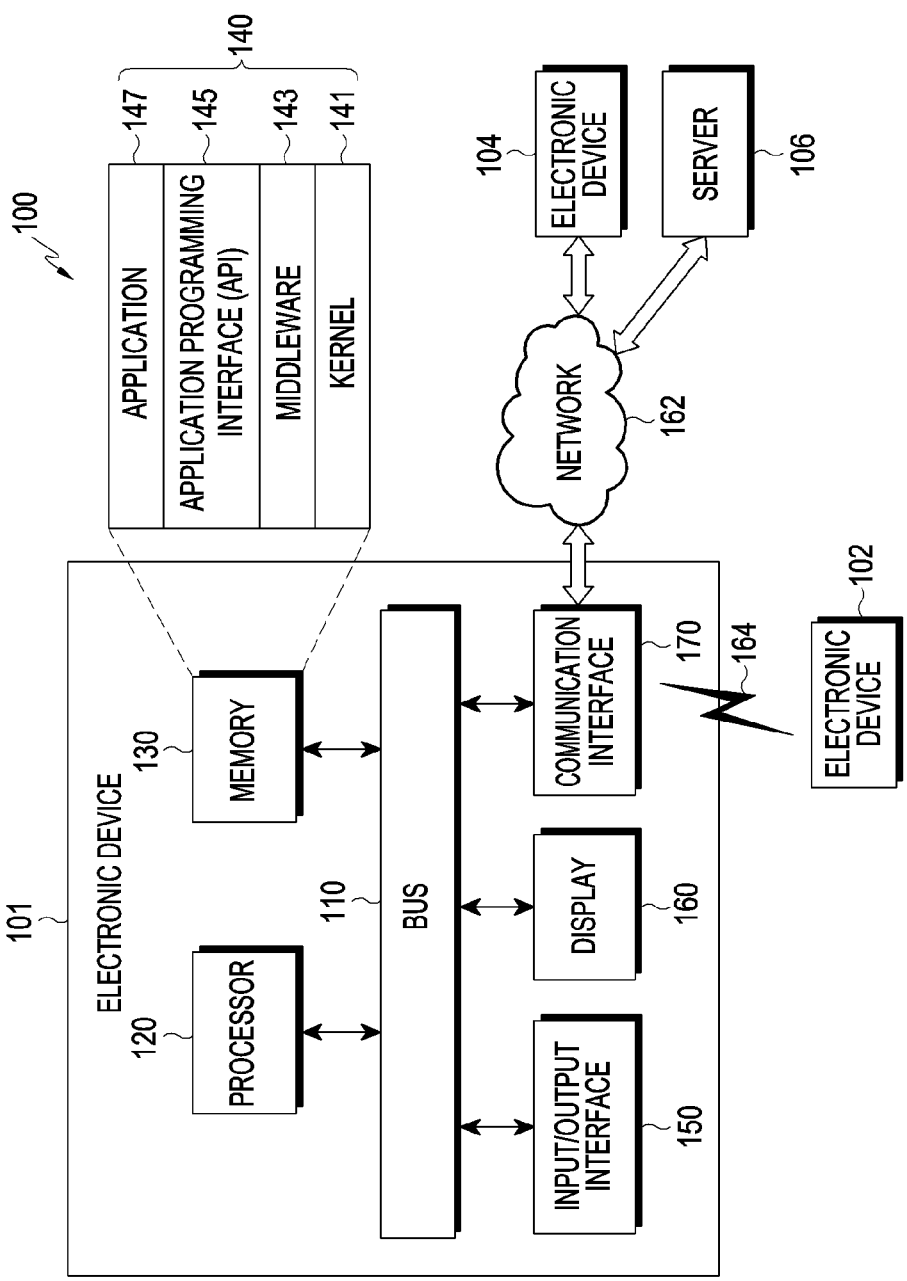
FIG. 1 illustrates a network environment including an electronic device according to various embodiments of the present disclosure.

Hereinafter, various embodiments of the present disclosure will be disclosed with reference to the accompanying drawings. Embodiments and terms used therein are not intended to limit the present disclosure to particular embodiments, and it should be construed as including various modifications, equivalents, and/or alternatives according to the embodiments of the present disclosure. With regard to the description of the drawings, similar reference numerals may be used to refer to similar or related elements. It is to be understood that a singular form of a noun corresponding to an item may include one or more of the things, unless the relevant context clearly indicates otherwise. In the present disclosure, an expression such as "A or B," "at least one of A or/and B," or "one or more of A or/and B" may include all possible combinations of together listed items. Expressions such as "first," "second," "primarily," or "secondary," used herein may represent various elements regardless of order and/or importance and do not limit corresponding elements. When it is described that an element (such as a first element) is "operatively or communicatively coupled with/to" or "connected" to another element (such as a second element), the element can be directly connected to the other element or can be connected to the other element through another element (e.g., a third element).

An expression "configured to (or set)" used in the present disclosure may be replaced with, for example, "suitable for," "having the capacity to," "adapted to," "made to," "capable of," or "designed to" according to a situation. Alternatively, in some situation, an expression "apparatus configured to" may mean that the apparatus "can" operate together with another apparatus or component. For example, a phrase "a processor configured (or set) to perform A, B, and C" may be a dedicated processor (e.g., an embedded processor) for performing a corresponding operation or a generic-purpose processor (such as a central processing unit (CPU) or an application processor) that can perform a corresponding operation by executing at least one software program stored at a memory device.

Examples of the electronic device according to embodiments of the present disclosure may include at least one of a smartphone, a tablet personal computer (PC), a mobile phone, a video phone, an e-book reader, a desktop PC, a laptop computer, a netbook computer, a workstation, a server, a personal digital assistant (PDA), a portable multimedia player (PMP), a MP3 player, a medical device, a camera, or a wearable device. The wearable device may include at least one of an accessory-type device (e.g., a watch, a ring, a bracelet, an anklet, a necklace, glasses, contact lenses, or a head-mounted device (HMD)), a fabric- or clothes-integrated device (e.g., electronic clothes), a body attaching-type device (e.g., a skin pad or tattoo), or a body implantable device. In some embodiments, the electronic device may include, for example, at least one of a television (TV), a digital video disk (DVD) player, audio equipment, a refrigerator, an air conditioner, a vacuum cleaner, an oven, a microwave oven, a laundry machine, an air cleaner, a set-top box, a home automation control panel, a security control panel, a media box (e.g., Samsung HomeSync™, Apple TV™, or Google TV™), a game console (e.g., Xbox™, PlayStation™, etc.), an electronic dictionary, an electronic key, a camcorder, or an electronic frame.

In other embodiments, the electronic device may include at least one of various medical equipment (for example, magnetic resonance angiography (MRA), magnetic resonance imaging (MRI), computed tomography (CT), an imaging device, or an ultrasonic device), a navigation system, a global positioning system (GPS) receiver, an event data recorder (EDR), a flight data recorder (FDR), a vehicle infotainment device, electronic equipment for ships (e.g., a navigation system and gyro compass for ships), avionics, a security device, a vehicle head unit, an industrial or home robot, a drone, an automatic teller's machine (ATM), a Point of Sales (POS), or Internet of things (e.g., electric bulbs, various sensors, electricity or gas meters, sprinkler devices, fire alarm devices, thermostats, streetlights, toasters, exercise machines, hot-water tanks, heaters, boilers, and so forth). According to some embodiments, the electronic device may include a part of a furniture, building/structure or a part of a vehicle, an electronic board, an electronic signature receiving device, a projector, and various measuring instruments (e.g., a water, electricity, gas, electric wave measuring device, etc.). According to various embodiments, the electronic device may be flexible or may be a combination of two or more of the above-described various devices. According to an embodiment of the disclosure, the electronic device is not limited to those described above. Herein, the term "user" used in various embodiments of the present disclosure may refer to a person who uses the electronic device or a device using the electronic device.

Referring to FIG. 1, an electronic device 101 in a network environment 100 according to various embodiments is disclosed. The electronic device 101 may include a bus 110, a processor 120, a memory 130, an input/output (I/O) interface 150, a display 160, and a communication interface 170. In some embodiments, the electronic device 101 may not include at least one of the foregoing elements or may further include other elements. The bus 110 may include a circuit for connecting, e.g., the elements 110 to 2170 and delivering communication (e.g., a control message or data) between the elements 110 to 170. The processor 120 may include one or more of a central processing unit (CPU), an application processor (AP), and a communication processor (CP). The processor 120 performs operations or data processing for control and/or communication of, for example, at least one other elements of the electronic device 101.

The memory 130 may include a volatile and/or nonvolatile memory. The memory 130 may store, for example, instructions or data associated with at least one other elements of the electronic device 101. According to an embodiment, the memory 130 may store software and/or a program 140. The program 140 may include at least one of, for example, a kernel 141, middleware 143, an application programming interface (API) 145, and/or an application program (or "application") 147, and the like. At least some of the kernel 141, the middleware 143, or the API 145 may be referred to as an operating system (OS). The kernel 141 may control or manage, for example, system resources (e.g., the bus 110, the processor 120, or the memory 130, etc.) used to execute operations or functions implemented in other programs (e.g., the middleware 143, the API 145, or the application program 147). In addition, the kernel 141 provides an interface through which the middleware 143, the API 145, or the application program 147 accesses separate components of the electronic device 101 to control or manage the system resources.

The middleware 143 may work as an intermediary for allowing, for example, the API 145 or the application program 147 to exchange data in communication with the kernel 141. In addition, the middleware 143 may process one or more task requests received from the application program 147 based on priorities. For example, the middleware 143 may give a priority for using a system resource (e.g., the bus 110, the processor 120, or the memory 130, etc.) of the electronic device 101 to at least one of the application programs 147, and may process the one or more task requests. The API 145 is an interface used for the application 147 to control a function provided by the kernel 141 or the middleware 143, and may include, for example, at least one interface or function (e.g., an instruction) for file control, window control, image processing or character control. The I/O interface 150 may deliver, for example, an instruction or data input from a user or another external device to other component(s) of the electronic device 101, or output an instruction or data received from other component(s) of the electronic device 101 to a user or another external device.

The display 160 may include, for example, a liquid crystal display (LCD), a light emitting diode (LED) display, an organic light emitting diode (OLED) display, a microelectromechanical system (MEMS) display, or an electronic paper display. The display 160 may, for example, display various contents (e.g., a text, an image, video, an icon, and/or a symbol, etc.) to users. The display 160 may include a touch screen, and receives a touch, a gesture, proximity, or a hovering input, for example, by using an electronic pen or a part of a body of a user.

The communication interface 170 establishes communication between the electronic device 101 and an external device (e.g., a first external electronic device 102, a second external electronic device 104, or a server 106). For example, the communication interface 170 may be connected to a network 162 through wireless communication or wired communication to communicate with an external device (e.g., the second external electronic device 104 or the server 106).

Wireless communication may include a cellular communication protocol using at least one of, for example, long-term evolution (LTE), LTE advance (LTE-A), code division multiple access (CDMA), wideband CDMA (WCDMA), universal mobile telecommunications system (UMTS), wireless broadband (WiBro), global system for mobile communications (GSM), and so forth. According to an embodiment, the wireless communication may include at least one of Wireless Fidelity (WiFi), Bluetooth, Bluetooth Low Energy (BLE), Zigbee, near field communication (NFC), magnetic secure transmission (MST), radio frequency (RF), or a body area network (BAN). According to an embodiment, the wireless communication may include GNSS. The GNSS may include, for example, at least one of a global positioning system (GPS), a global navigation satellite system (Glonass), a Beidou navigation satellite system ("Beidou"), or Galileo, the European global satellite-based navigation system. Hereinbelow, "GPS" may be used interchangeably with "GNSS". The wired communication may include, for example, at least one of a universal serial bus (USB), a high definition multimedia interface (HDMI), a recommended standard 232 (RS-232), power line communication, or a plain old telephone service (POTS), and so forth. The network 162 may include a telecommunications network, for example, at least one of a computer network (e.g., a local area network (LAN) or a wide area network (WAN)), Internet, or a telephone network.

Each of the first external electronic device 102 and the second external electronic device 104 may be a device of the same type as or a different type than the electronic device 101. According to various embodiments, some or all of operations performed by the electronic device 101 may be performed in another electronic device or a plurality of electronic devices (e.g., the electronic device 102,104 or the server 106). According to an embodiment, when the electronic device 101 has to perform a function or a service automatically or at a request, the electronic device 101 may request another device (e.g., the electronic devices 102 or 104 or the server 106) to perform at least some functions associated with the function or the service instead of or in addition to executing the function or the service. The another electronic device (e.g., the electronic device 102 or 104 or the server 106) may execute the requested function or additional function and deliver the execution result to the electronic device 101. The electronic device 101 may then process or further process the received result to provide the requested function or service. To that end, a cloud computing, distributed computing, or client-server computing technology may be used, for example.

A wearable electronic device according to various embodiments of the present disclosure includes a light source, at least one lens, an optical surface positioned on a first side of the at least one lens, and a camera configured to receive light, which is output from the light source and scattered by a subject located on a second side of the at least one lens, through the at least one lens and the optical surface.

The wearable electronic device according to various embodiments of the present disclosure may further include a processor configured to identify an image corresponding to the light received by the camera, in which the processor is further configured to control at least one of the light source, the at least one lens, the optical surface, and the camera, based on the identified image.

The wearable electronic device according to various embodiments of the present disclosure may further include an input/output interface configured to electrically connect the wearable electronic device to a processor provided in a mobile electronic device attachable to or detachable from the wearable electronic device, in which the processor is further configured to identify an image corresponding to the light received by the camera and to control at least one of the light source, the at least one lens, the optical surface, and the camera, based on the identified image.

In the wearable electronic device according to various embodiments of the present disclosure, the processor may be further configured to control the light source to irradiate at least one infrared light to the subject, to control the camera to receive the at least one infrared light reflected from the optical surface in correspondence to the at least one infrared light irradiated to the subject, and to obtain information about the subject based on the at least one infrared light received by the camera.

The wearable electronic device according to various embodiments of the present disclosure may further include at least one sensor configured to detect a distance between the subject and the wearable electronic device, in which the processor is further configured to periodically receive information about the distance between the subject and the wearable electronic device from the at least one sensor, to identify a motion of the subject by using the received information about the distance, and to obtain information about the subject based on the identified motion of the subject.

The wearable electronic device according to various embodiments of the present disclosure may further include at least one display on an outer side of the wearable electronic device, in which the processor is further configured to display an image corresponding to the light received by the camera on the at least one display.

In the wearable electronic device according to various embodiments of the present disclosure, the light source may be positioned between the subject and the at least one lens.

In the wearable electronic device according to various embodiments of the present disclosure, the light source may be positioned between the optical surface and the at least one lens.

In the wearable electronic device according to various embodiments of the present disclosure, the at least one lens may be positioned between the subject and the optical surface and include a convex lens.

In the wearable electronic device according to various embodiments of the present disclosure, the subject may include an eye of a user wearing the wearable electronic device, and the camera may be further configured to obtain an image of the subject based on the received light.

The wearable electronic device according to various embodiments of the present disclosure may further include a display positioned on the first side, in which the optical surface is positioned on the display.

In the wearable electronic device according to various embodiments of the present disclosure, the optical surface may be positioned on a display provided in the mobile electronic device attachable to or detachable from the wearable electronic device.

In the wearable electronic device according to various embodiments of the present disclosure, the optical surface may include a filter configured to penetrate visible light and reflect infrared light.

In the wearable electronic device according to various embodiments of the present disclosure, the camera may include an infrared camera configured to infrared light among light rays reflected from the optical surface.

Figure 2:
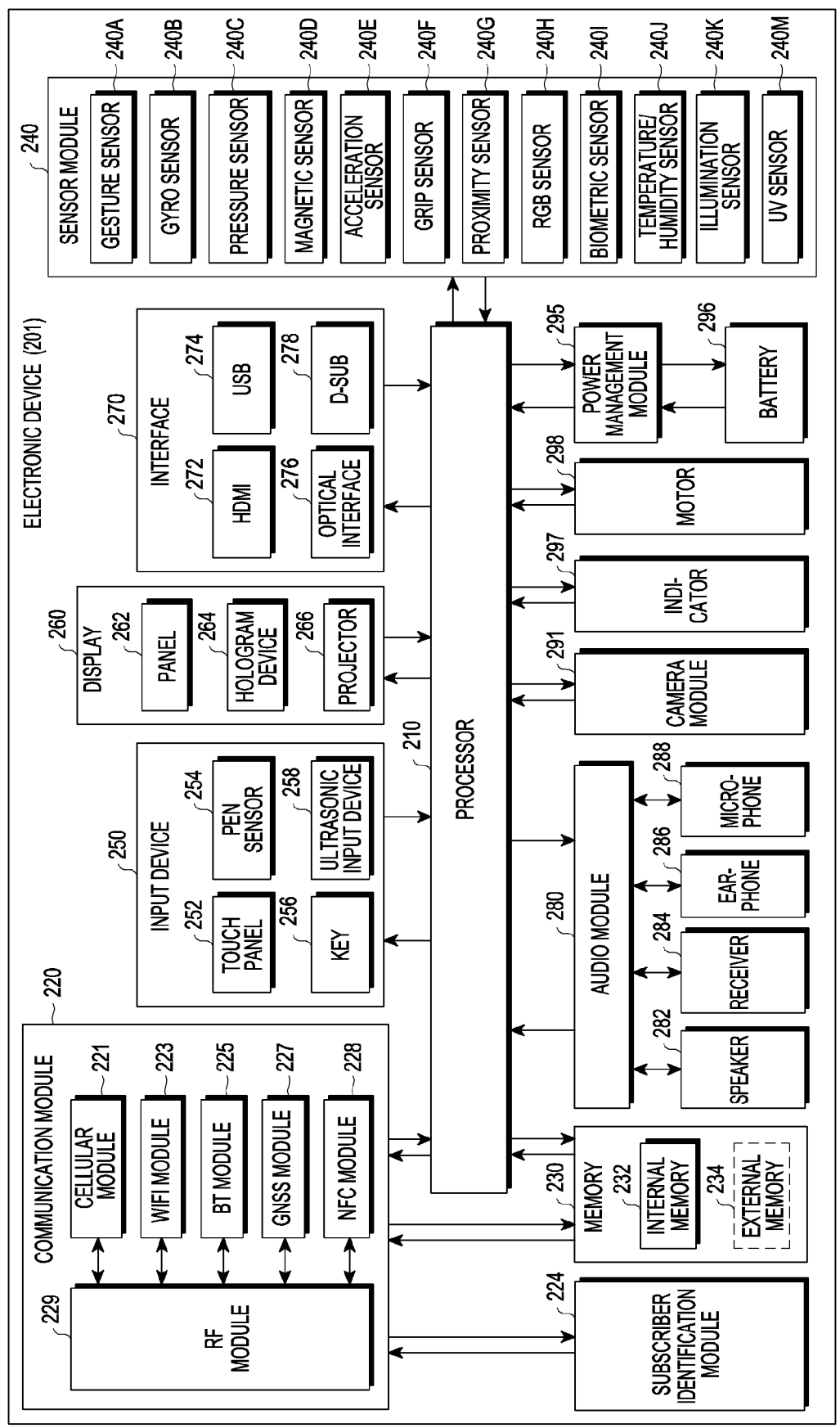
FIG. 2 is a block diagram of an electronic device according to various embodiments of the present disclosure.

FIG. 2 is a block diagram of an electronic device 201 according to various embodiments. The electronic device 201 may form the entire electronic device 101 illustrated in FIG. 1 or a part of the electronic device 101 illustrated in FIG. 1. The electronic device 201 may include one or more processors (e.g., application processors (APs)) 210, a communication module 220, a subscriber identification module (SIM) 224, a memory 230, a sensor module 240, an input device 250, a display 260, an interface 270, an audio module 280, a camera module 291, a power management module 295, a battery 296, an indicator 297, and a motor 298.

The processor 210 controls multiple hardware or software components connected to the processor 210 by driving an operating system (OS) or an application program, and performs processing and operations with respect to various data. The processor 210 may be implemented with, for example, a system on chip (SoC). According to an embodiment, the processor 210 may include a GPU and/or an image signal processor. The processor 210 may include at least some of the elements illustrated in FIG. 2 (e.g., the cellular module 221). The processor 210 loads a command or data received from at least one of other elements (e.g., a non-volatile memory) into a volatile memory to process the command or data, and stores result data in the non-volatile memory.

The communication module 220 may have a configuration that is the same as or similar to the communication interface 170. The communication module 220 may include, for example, the cellular module 221, a WiFi module 223, a Bluetooth (BT) module 225, a GNSS module 227, an NFC module 228, and a radio frequency (RF) module 229. The cellular module 221 may provide, for example, a voice call, a video call, a text service, or an Internet service over a communication network. According to an embodiment, the cellular module 221 identifies and authenticates the electronic device 201 in a communication network by using the SIM 224 (e.g., a SIM card). According to an embodiment, the cellular module 221 performs at least one of functions that may be provided by the processor 210. According to an embodiment, the cellular module 221 may include a communication processor (CP). According to some embodiment, at least some (e.g., two or more) of the cellular module 221, the WiFi module 223, the BT module 225, the GNSS module 227, or the NFC module 228 may be included in one integrated chip (IC) or IC package. The RF module 229 may, for example, transmit and receive a communication signal (e.g., an RF signal). The RF module 229 may include a transceiver, a power amp module (PAM), a frequency filter, a low noise amplifier (LNA), or an antenna. According to another embodiment, at least one of the cellular module 221, the WiFi module 223, the BT module 225, the GNSS module 227, or the NFC module 228 may transmit and receive an RF signal through the separate RF module. The SIM 224 may, for example, include a card including a SIM or an embedded SIM, and may include unique identification information (e.g., an integrated circuit card identifier (ICCID) or subscriber information (e.g., an international mobile subscriber identity (IMSI)).

The memory 230 (e.g., the memory 130) may, for example, include an internal memory 232 or an external memory 234. The internal memory 232 may, for example, include at least one of a volatile memory (e.g., dynamic random access memory (DRAM), static RAM (SRAM), or synchronous dynamic RAM (SDRAM), etc.), a non-volatile memory (e.g., one time programmable read only memory (OTPROM)), programmable ROM (PROM), erasable and programmable ROM (EPROM), electrically erasable and programmable ROM (EEPROM), etc.), mask ROM, flash ROM, a flash memory, hard drive or a solid state drive (SSD). The external memory 234 may include flash drive, for example, compact flash (CF), secure digital (SD), micro-SD, mini-SD, extreme Digital (xD), a multi-media card (MMC), or a memory stick. The external memory 234 may be functionally or physically connected with the electronic device 201 through various interfaces.

The sensor module 240 measures physical quantity or senses an operation state of the electronic device 201 to convert the measured or sensed information into an electric signal. The sensor module 240 may, for example, include at least one of a gesture sensor 240A, a gyro sensor 240B, a pressure sensor 240C, a magnetic sensor 240D, an acceleration sensor 240E, a grip sensor 240F, a proximity sensor 240G, a color sensor 240H (e.g., red/green/blue (RGB) sensor), a biometric sensor 240I, a temperature/humidity sensor 240J, an illumination sensor 240K, or a ultraviolet (UV) sensor 240M. Additionally or alternatively, the sensor module 240 may include an E-nose sensor (not shown), an electromyography (EMG) sensor (not shown), an electroencephalogram (EEG) sensor (not shown), an electrocardiogram (ECG) sensor (not shown), an infrared (IR) sensor, an iris sensor, and/or a fingerprint sensor. The sensor module 240 may further include a control circuit for controlling at least one sensor included therein. In some embodiment, the electronic device 201 may further include a processor configured to control the sensor module 240 as part of or separately from the processor 210, to control the sensor module 240 during a sleep state of the processor 210.

The input device 250 may include, for example, a touch panel 252, a (digital) pen sensor 254, a key 256, or an ultrasonic input device 258. The touch panel 252 may use at least one of a capacitive type, a resistive type, an IR type, or an ultrasonic type. In addition, the touch panel 252 may further include a control circuit. The touch panel 252 may further include a tactile layer to provide tactile reaction to the user. The (digital) pen sensor 254 may include a recognition sheet which is a part of the touch panel 252 or a separate recognition sheet. The key 256 may also include a physical button, an optical key, or a keypad. The ultrasonic input device 258 senses ultrasonic waves generated by an input means through a microphone (e.g., the microphone 288) and checks data corresponding to the sensed ultrasonic waves.

The display 260 (e.g., the display 160) may include a panel 262, a hologram device 264, a projector 266, and/or a control circuit for controlling them. The panel 262 may be implemented to be flexible, transparent, or wearable. The panel 262 may be configured with the touch panel 252 in one module. According to an embodiment, the panel 262 may include a pressure sensor (or a "force sensor", interchangeably used hereinafter) capable of measuring a strength of a pressure by a user's touch. The pressure sensor may be implemented integrally with the touch panel 252 or may be implemented as one or more sensors separate from the touch panel 252. The hologram device 264 may show a stereoscopic image in the air by using interference of light. The projector 266 may display an image onto a screen through projection of light. The screen may be positioned inside or outside the electronic device 201.

The interface 270 may include an HDMI 272, a USB 274, an optical interface 276, or a D-subminiature (D-sub) 278. The interface 270 may be included in the communication interface 170 illustrated in FIG. 1. Additionally or alternatively, the interface 270 may include a mobile high-definition link (MHL) interface, an SD/multi-media card (MMC) interface, or an Infrared Data Association (IrDA) interface.

The audio module 280 may bi-directionally convert sound and an electric signal. At least one element of the audio module 280 may be included in the input/output interface 145 illustrated in FIG. 1. The audio module 280 may process sound information input or output through the speaker 282, the receiver 284, the earphone 286, or the microphone 288.

The camera module 291 is, for example, a device capable of capturing a still image or a moving image, and according to an embodiment, may include one or more image sensors (e.g., a front sensor or a rear sensor), a lens, an image signal processor (ISP), or a flash (e.g., an LED, a xenon lamp, etc.). The power management module 295 manages power of the electronic device 201. According to an embodiment, the power management module 295 may include a power management integrated circuit (PMIC), a charger IC, or a battery fuel gauge. The PMIC may have a wired and/or wireless charging scheme. The wireless charging scheme may include a magnetic-resonance type, a magnetic induction type, and an electromagnetic type, and may further include an additional circuit for wireless charging, for example, a coil loop, a resonance circuit, or a rectifier. The battery gauge may measure the remaining capacity of the battery 296 or the voltage, current, or temperature of the battery 296 during charging. The battery 296 may include, for example, a rechargeable battery and/or a solar battery. The indicator 297 displays a particular state, for example, a booting state, a message state, or a charging state, of the electronic device 201 or a part thereof (e.g., the processor 210). The motor 298 may convert an electric signal into mechanical vibration or generates vibration or a haptic effect. The electronic device 201 may include a device for supporting the mobile TV (e.g., a GPU) to process media data according to a standard such as digital multimedia broadcasting (DMB), digital video broadcasting (DVB), or mediaFlo™. Each of the foregoing elements described herein may be configured with one or more components, names of which may vary with a type of the electronic device. In various embodiments, some components of the electronic device (e.g., the electronic device 201) may be omitted or may further include other elements, and some of the components may be coupled to form one entity and identically perform functions of the components before being coupled.

Figure 3:
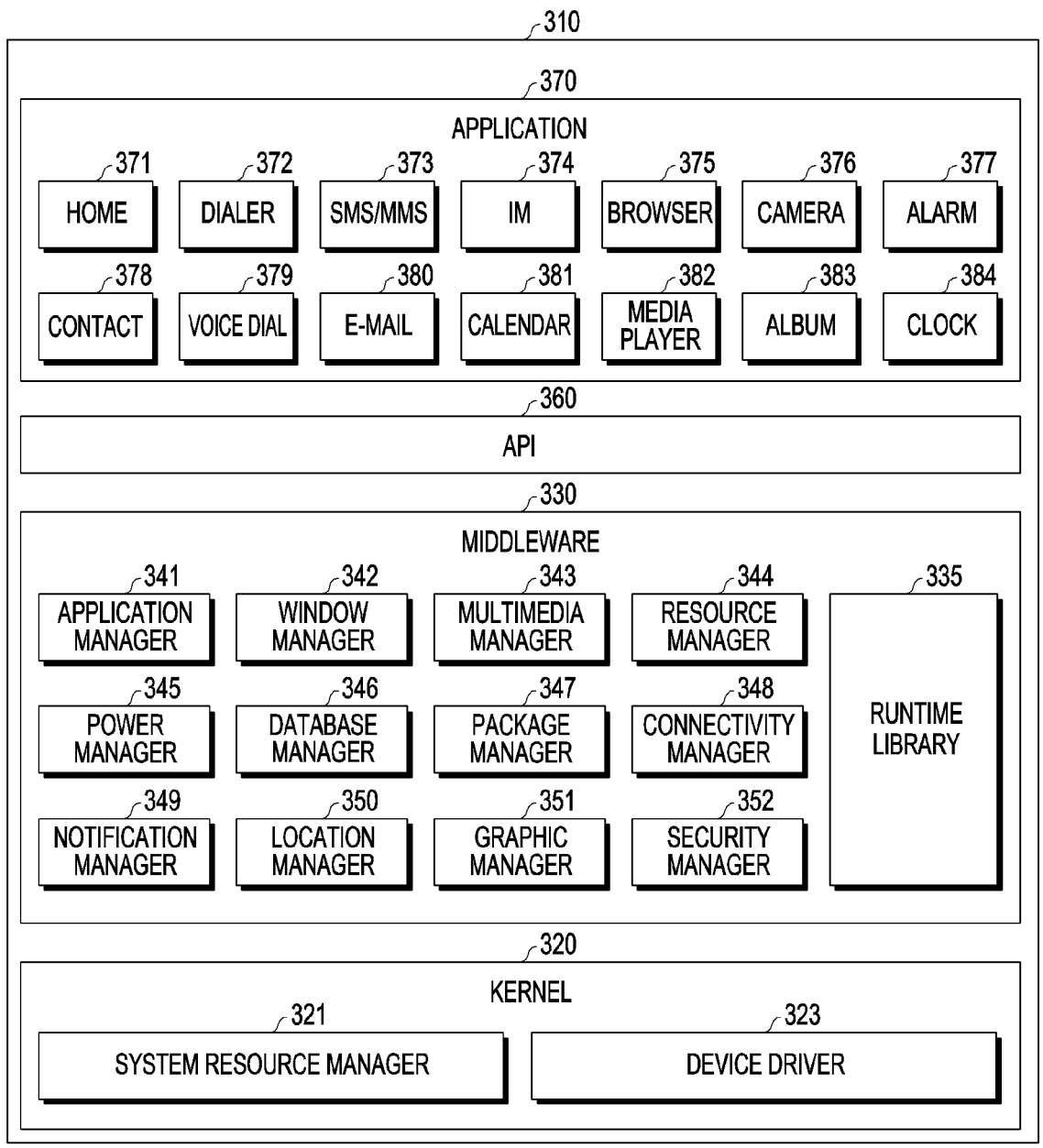
FIG. 3 is a block diagram of a programming module according to various embodiments of the present disclosure.

FIG. 3 is a block diagram of a programming module according to various embodiments. According to an embodiment, a programming module 310 (e.g., the program 140) may include an OS for controlling resources associated with an electronic device (e.g., the electronic device 101) and/or various applications (e.g., the application program 147) executed on the OS. The OS may include, for example, Android™, iOS™, Windows™, Symbian™, Tizen™, or Bada™. Referring to FIG. 3, the programming module 310 may include a kernel 320 (e.g., the kernel 141), middleware 330 (e.g., the middleware 143), an application programming interface (API) 360 (e.g., the API 145), and/or an application 370 (e.g., the application program 147). At least a part of the programming module 310 may be preloaded on an electronic device or may be downloaded from an external device (e.g., the electronic device 102 or 104, or the server 106).

The kernel 320 may include a system resource manager 321 and/or a device driver 323. The system resource manager 321 may perform control, allocation, retrieval of system resources, and so forth. According to an embodiment, the system resource manager 321 may include a process management unit, a memory management unit, or a file system management unit. The device driver 323 may include, for example, a display driver, a camera driver, a Bluetooth driver, a shared memory driver, a USB driver, a keypad driver, a WiFi driver, an audio driver, or an inter-process communication (IPC) driver. The middleware 330 may include provide functions that the application 370 commonly requires or provide various functions to the application 370 through the API 360 to allow the application 370 to use a limited system resource in an electronic device. According to an embodiment, the middleware 330 may include at least one of a runtime library 335, an application manager 341, a window manager 342, a multimedia manager 343, a resource manager 344, a power manager 345, a database manager 346, a package manager 347, a connectivity manager 348, a notification manager 349, a location manager 350, a graphic manager 351, or a security manager 352.

The runtime library 335 may include a library module that a compiler uses to add a new function through a programming language while the application 370 is executed. The runtime library 335 performs input/output management, memory management, or calculation function processing. The application manager 341 manages a life cycle of the applications 370. The window manager 342 manages a graphic user interface (GUI) resource used in a screen. The multimedia manager 343 recognizes a format necessary for playing media files and performs encoding or decoding on a media file by using a codec appropriate for a corresponding format. The resource manager 344 manages a source code or a memory space of the applications 370. The power manager 345 manages a battery or power and provides power information necessary for an operation of the electronic device. According to an embodiment, the power manager 345 may operate with basic input/output system (BIOS). The database manager 346 generates, searches or changes a database used for at least one application among the applications 370. The package manager 347 manages the installation or update of an application distributed in a package file format.

The connectivity manager 348 manages a wireless connection. The notification manager 349 provides an event, e.g., an arriving message, an appointment, proximity notification, etc. The location manager 350 manages location information of an electronic device. The graphic manager 351 manages, for example, a graphic effect to be provided to a user or a user interface relating thereto. The security manager 352 provides, for example, system security or user authentication. According to an embodiment, the middleware 330 may further include a telephony manager for managing a voice or video call function of the electronic device or a middleware module forming a combination of functions of the above-described components. According to an embodiment, the middleware 330 provides a module specified for each type of an OS. Additionally, the middleware 330 may delete some of existing elements or add new elements dynamically. The API 360 may be provided as a set of API programming functions with a different configuration according to the OS. In the case of Android or iOS, for example, one API set may be provided by each platform, and in the case of Tizen, two or more API sets may be provided.

The application 370 may include one or more applications capable of providing a function, for example, a home application 371, a dialer application 372, a short messaging service/multimedia messaging service (SMS/MMS) application 373, an instant message (IM) application 374, a browser application 375, a camera application 376, an alarm application 377, a contact application 378, a voice dial application 379, an e-mail application 380, a calendar application 381, a media player application 382, an album application 383, a clock application 384, a health care application (e.g., an application for measuring an exercise amount, a blood sugar, etc.), or an environment information providing application (e.g., an application for providing air pressure, humidity, or temperature information or the like). According to an embodiment, the application 370 may include an information exchange application supporting information exchange between the electronic device and an external electronic device. The information exchange application may include, for example, a notification relay application for transferring specific information to the external electronic device or a device management application for managing the external electronic device. For example, the notification relay application may deliver notification information generated in another application of the electronic device to an external electronic device or may receive notification information from the external electronic device and provide the notification information to the user. The device management application may manage (e.g., install, remove, or update) a function (e.g., turn on/turn off of an external electronic device itself (or a part thereof) or control of brightness (or resolution) of a display) of an external device communicating with the electronic device, a service provided by an application operating in an external electronic device or provided by the external electronic device (e.g., a call service or a message service). According to an embodiment, the application 370 may include an application (e.g., device health care application of mobile medical equipment) designated according to an attribute of the external electronic device. According to an embodiment, the application 370 may include an application received from the external electronic device. The at least a part of the programming module 310 may be implemented (e.g., executed) by software, firmware, hardware (e.g., the processor 210), or a combination of two or more of them, and may include, for example, modules, programs, routines, sets of instructions, or processes for performing one or more functions.

Figure 4:
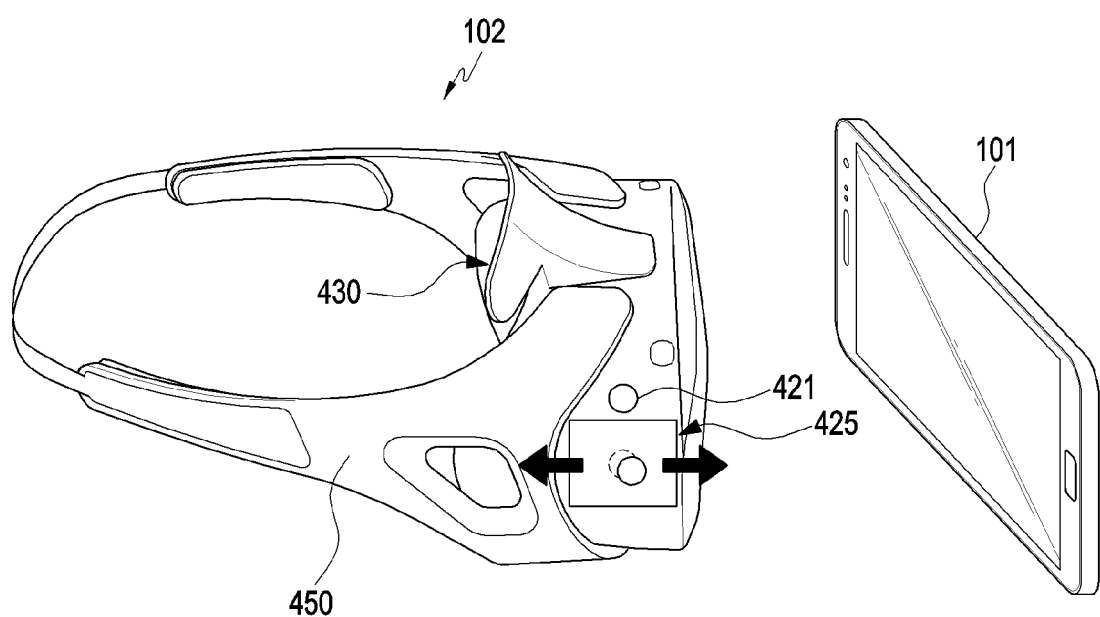
FIG. 4 is a perspective view illustrating an electronic device according to various embodiments of the present disclosure.

FIG. 4 is a perspective view illustrating an electronic device according to various embodiments of the present disclosure.

The electronic device 101 may include a display. The electronic device 101 may store a VR application. The VR application may be an application capable of providing visual data that is similar to reality to the user. In an embodiment, the VR application may display a left-eye image and a right-eye image respectively corresponding to both eyes of the user based on a stereoscopic scheme.

The electronic device 102 may be a head-mounted display (HMD). The HMD may be worn on a user's head and thus may be fixed onto the user's head in spite of the user's movement. The electronic device 101 may be coupled to the electronic device 102. As the user wears the electronic device 102 coupled to the electronic device 101, the user may observe the left-eye image and the right-eye image that are displayed on the display of the electronic device 101. The left-eye image and the right-eye image the user may observe may be enlarged through at least one lens (not shown) provided between the user's eyes and the display of the electronic device 101.

The electronic device 102 according to an embodiment may include a housing 450 provided to be worn on the user's head, a shielding portion 430 that is fixed on the housing 450 and provided in a region corresponding to positions of the user's eyes, and at least one input button 421 provided in a region of the housing 450. The electronic device 102 may include an input pad 425 capable of receiving a swipe input from the user.

The user may bring the eyes into close contact with the shielding portion 430, thus observing an image corresponding to the VR application provided from the electronic device 101 without interference from external light. In an embodiment, the shielding portion 430 may include at least one light source that irradiate light including a plurality of wavelengths toward the user's eyes. The light irradiated from the light source included in the shielding portion 430 may be scattered after reaching the eyes of the user wearing the electronic device 102, and the scattered light may be delivered to the display of the electronic device 101 after penetrating the lens provided between the user's eyes and the display of the electronic device 101.

The electronic device 101 may be coupled to the electronic device 102. The electronic device 101 may be wirelessly/wiredly connected with the electronic device 102. For example, the electronic device 101 may be connected with the electronic device 102 by using a universal serial bus (USB), but this is merely an example, and those of ordinary skill in the art may easily understand that there is no limitation as long as the connection enables data transmission and reception between the two devices 101 and 102. In another example, the electronic device 101 may be simply physically connected with the electronic device 102.

Figure 5:
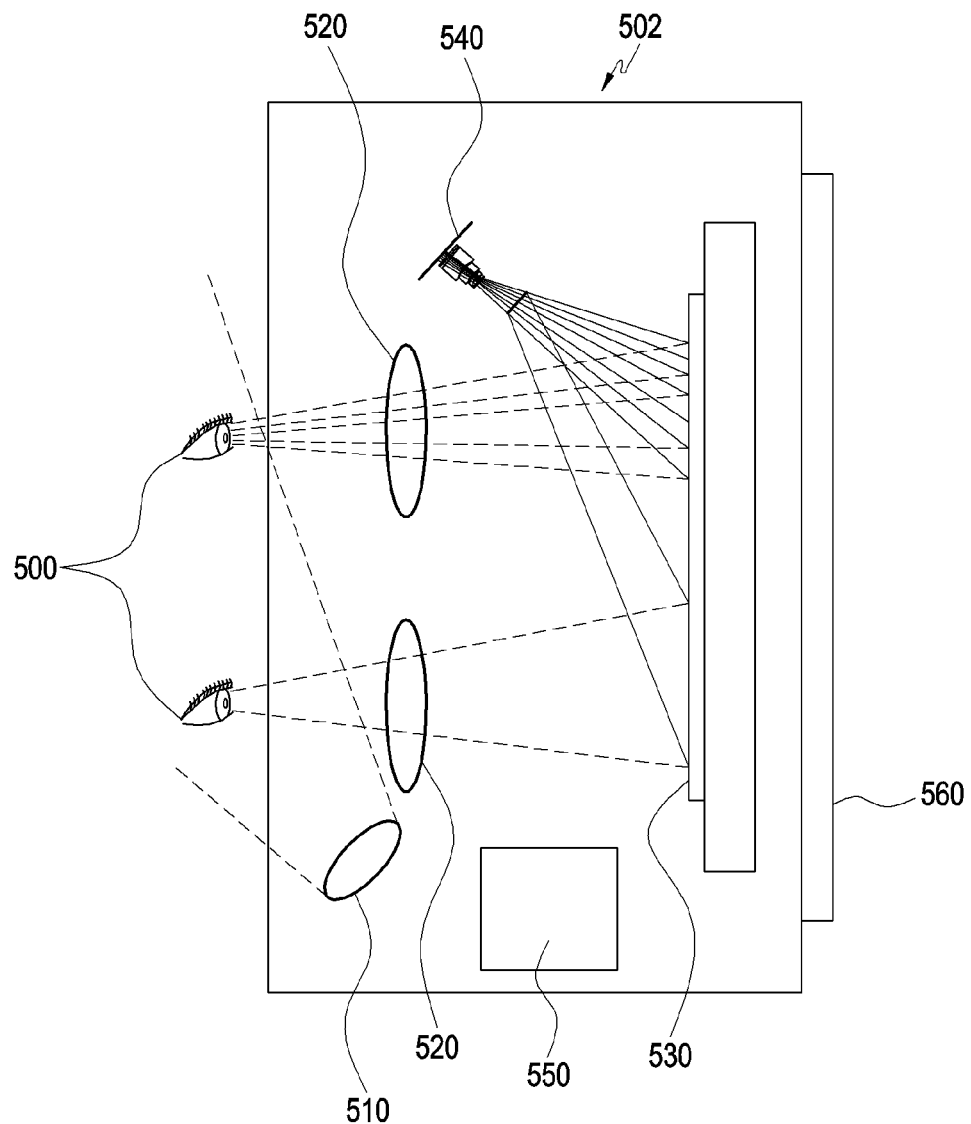
FIG. 5 is a view for describing a structure of an electronic device according to various embodiments of the present disclosure.

FIG. 5 is a view for describing a structure of an electronic device according to various embodiments of the present disclosure.

An electronic device 502 may be an HMD or a VR device. The electronic device 502 may include at least one of a light source 510 that irradiates light including a plurality of wavelengths to a subject 500, at least one lens 520 that refracts various light rays, an optical surface 530 that reflects an image, a camera 540 that captures an image, a processor 550, and a display 560. According to an embodiment, the subject 500 may include eyes of a user wearing the electronic device 502 and a surrounding area of the eyes.

The light source 510 may emit the light including the plurality of wavelengths. For example, the light source 510 may emit visible light. Alternatively, the light source 510 may emit infrared light having a wavelength (750~1000 nm) greater than that of red visible light or ultraviolet light having a wavelength (10~390 nm) less than that of violet visible light. The light source 510 may be mounted in an inside of the electronic device 502, and may irradiate light including at least one wavelength to a body part of the user wearing the electronic device 502. The light source 510 may be provided in any position to irradiate light toward the body part of the user wearing the electronic device 502.

According to an embodiment, the light source 510, which is an infrared light source capable of emitting infrared light, may irradiate light to the eyes of the user wearing the electronic device 502 and a surrounding area of the eyes. For example, when the user wears the electronic device 502, the eyes of the user may be positioned in the inside (e.g., the shielding portion 430) of the electronic device 502. At least one light irradiated from the light source 510 located in the inside of the electronic device 502 may be scattered after reaching the eyes of the user and the surrounding area of the eyes.

The at least one lens 520 may be provided in the inside of the electronic device 502. For example, the at least one lens 520 may be positioned between a surface on which the user wears the electronic device 502 (e.g., a surface on which the shielding portion 430 is positioned) and the optical surface 530 mounted in the inside of the electronic device 502. The light emitted from the optical surface 530 may be refracted through the at least one lens 520 and delivered to the user, and the light scattered from the user's eyes may be refracted through the at least one lens 520 and delivered to the optical surface 530. The at least one lens 520 may include a convex lens, but this is merely an example, and those of ordinary skill in the art may easily understand that there is no limitation as long as light is allowed to penetrate a medium.

The optical surface 530 may provide a virtual image to the user wearing the electronic device 502, and may include the display 160. For example, the optical surface 530 may emit visible light to provide a virtual image to the user wearing the electronic device 502.

According to an embodiment, the optical surface 530 may reflect light scattered from the body part of the user wearing the electronic device 502 or form an image corresponding to the body part of the user. The optical surface 530 may include a filter or a film for reflecting the light delivered from the subject 500 or forming the image corresponding to the subject 500. For example, infrared light irradiated from the light source 510 may be scattered after reaching the subject 500. The infrared light scattered in this way may penetrate the at least one lens 520 and be delivered to the optical surface 530. In the case that the filter or film included in the optical surface 530 reflects infrared light and absorbs light other than infrared light, the optical surface 530 may selectively reflect infrared light among a plurality of light rays delivered thereto. The optical surface 530 including the filter or film reflecting infrared light may reflect an image associated with the subject 500 to which infrared light is irradiated, and may not reflect light other than infrared light, such as visible light, etc., emitted from the optical surface 530. The optical surface 530 according to an embodiment may include a filter or a film of a transparent material or a semi-transparent material (e.g., a hot mirror) capable of selectively reflecting infrared light or forming an image based on infrared light.

The camera 540 may capture an image based on at least one light reflected through the optical surface 530 and may include the camera module 291. According to an embodiment, the camera 540 may be configured to selectively capture an image based on light of a particular wavelength. For example, the camera 540 may include an infrared camera that capture an image composed of infrared light.

According to an embodiment, the infrared camera may include a filter capable of reflecting or absorbing visible light emitted from the optical surface 530 and thus may selectively obtain an image composed of the infrared light reflected from the optical surface 530. The camera 540 may capture an image corresponding to the eyes of the user of the electronic device 502 or a surrounding area of the eyes in which the image has been reflected from the optical surface 530 based on infrared light. When capturing the image using a high-pixel camera, the camera 540 may obtain precise information regarding the user's eyes such as wrinkles around the user's eyes or twitches of the eyes, etc.

The processor 550 may be included in the electronic device 502 to control an operation or configuration of at least one of the light source 510, the at least one lens 520, the optical surface 530, the camera 540, and the display 560. For example, when irradiating infrared light toward the eyes of the user wearing the electronic device 502, the processor 550 may control the light source 510 to adjust the intensity of infrared light or a time during which the infrared light is irradiated, etc. In addition, the processor 550 may adjust a position of the at least one lens 520 to control a refractive index, etc. In addition, the processor 550 may also control an image or video displayed through the optical surface 530. In addition, the processor 550 may control the camera 540 to obtain at least one image reflected from the optical surface 530. In addition, the processor 550 may display at least one image, etc., obtained through the camera 540, by using the display 560 provided on an outer side of the electronic device 502.

The display 560 may be provided on the outer side of the electronic device 502. For example, the display 560 may be provided on a surface that opposes the surface on which the user wears the electronic device 502 (e.g., the surface on which the shielding portion 430 is positioned) to provide an image to another person facing the user wearing the electronic device 502.

Although it is illustrated in FIG. 5 that light penetrating a convex lens is refracted outward, this illustration is merely for convenience of a description. A spherical shape of the lens has been selected to simply indicate the lens, and those of ordinary skill in the art may easily understand that there is no limitation in a type of a spherical surface of the lens, an arranged position of the lens, and the number of lenses as long as the light scattered from the subject 500 is allowed to travel toward the optical surface 530.

Figure 6:
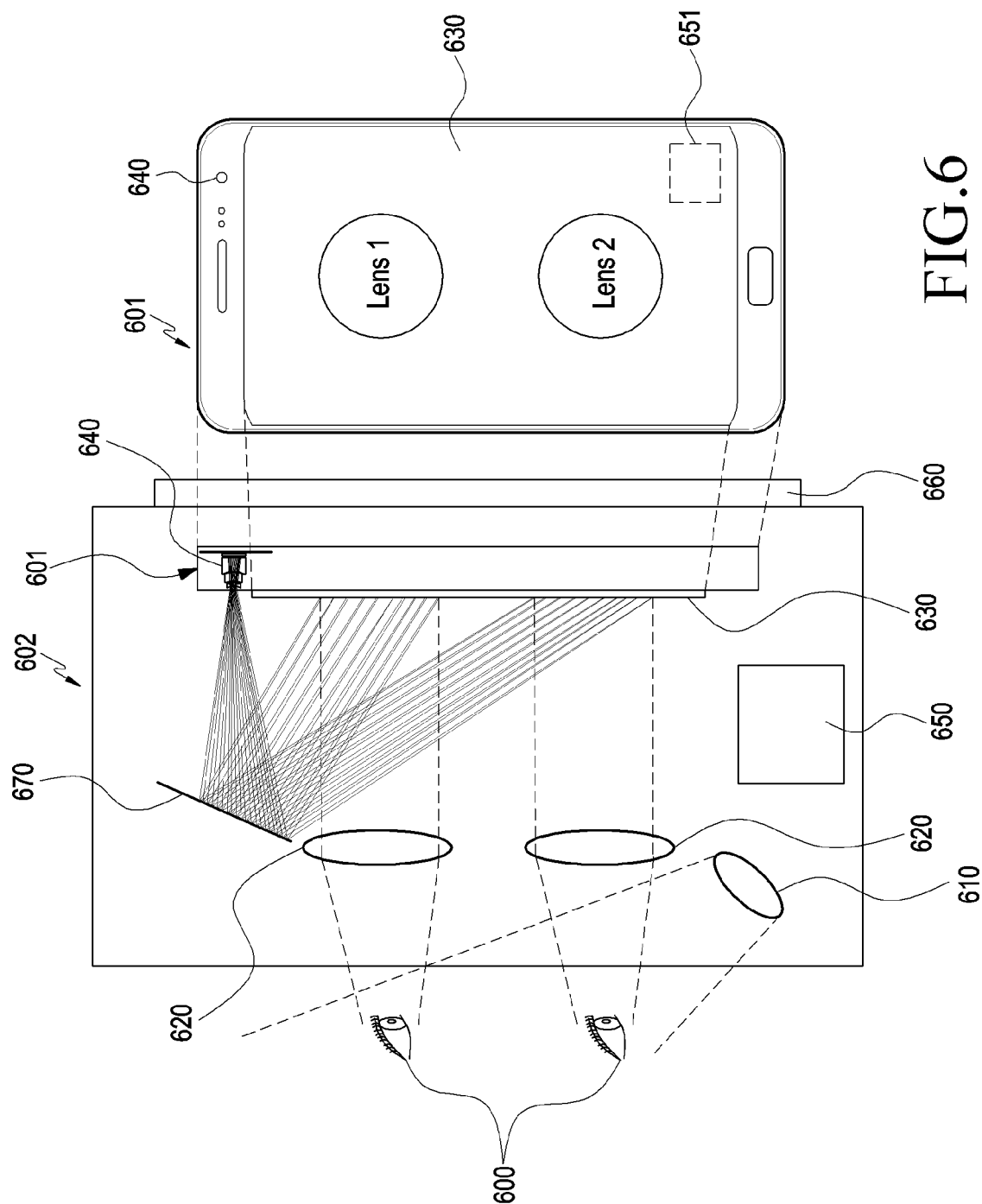
FIG. 6 is a view for describing a structure of an electronic device according to various embodiments of the present disclosure.

FIG. 6 is a view for describing a structure of an electronic device according to various embodiments of the present disclosure.

An electronic device 601 may include at least one of an optical surface 630 that reflects an image, a camera 640 that captures an image, or a processor 651. The optical surface 630 may include the display 160, and the camera 640 may include the camera module 291.

An electronic device 602 may be an HMD or a VR device. The electronic device 602 may include at least one of a light source 610 that irradiates light including a plurality of wavelengths to a subject 600, at least one lens 620 that refracts various light rays, a processor 650, a display 660, and a reflective mirror 670.

The electronic device 601 may be coupled to the electronic device 602. As the user wears the electronic device 602 coupled to the electronic device 601, the user may observe a left-eye image Lens 1 and a right-eye image Lens 2 that are displayed on the optical surface 630 (e.g., the display 160) of the electronic device 601.

The light source 610 of the electronic device 602 may emit the light including the plurality of wavelengths. For example, the light source 610 may emit visible light. The light source 510 may emit infrared light having a wavelength (750~1000 nm) greater than that of red visible light or ultraviolet light having a wavelength (10~390 nm) less than that of violet visible light. The light source 610 may be mounted in an inside of the electronic device 602, and may irradiate light including at least one wavelength to a body part of the user wearing the electronic device 602. The light source 610 may be provided in any position to irradiate light toward the body part of the user wearing the electronic device 602.

According to an embodiment, the light source 610, which is an infrared light source capable of emitting infrared light, may irradiate light to the eyes of the user wearing the electronic device 602 and a surrounding area of the eyes. For example, when the user wears the electronic device 602, the eyes of the user may be positioned in the inside (e.g., the shielding portion 430) of the electronic device 602. At least one light irradiated from the light source 610 located in the inside of the electronic device 602 may be scattered after reaching the eyes of the user and the surrounding area of the eyes.

The at least one lens 620 of the electronic device 602 may be provided in the inside of the electronic device 602. For example, the at least one lens 620 may be positioned between a surface on which the user wears the electronic device 602 (e.g., a surface on which the shielding portion 430 is positioned) and the optical surface 630 of the electronic device 601 coupled to the electronic device 602. The light emitted from the optical surface 630 of the electronic device 601 may be refracted through the at least one lens 620 and delivered to the user, and the light scattered from the user's eyes may be refracted through the at least one lens 620 and delivered to the optical surface 630. The at least one lens 620 may include a convex lens, but this is merely an example, and those of ordinary skill in the art may easily understand that there is no limitation as long as light is allowed to penetrate a medium.

The optical surface 630 of the electronic device 601 may provide a virtual image to the user wearing the electronic device 602, and may include the display 160. For example, the electronic device 601 may be physically or electrically coupled to the electronic device 602 to provide a virtual image to the user wearing the electronic device 602 through the optical surface 630 of the electronic device 601.

According to an embodiment, the optical surface 630 of the electronic device 601 may reflect light scattered from the body part of the user wearing the electronic device 602 or form an image corresponding to the body part of the user. The optical surface 630 may include a filter or a film for reflecting the light delivered from the subject 600 or forming the image corresponding to the subject 600. For example, infrared light irradiated from the light source 610 may be scattered after reaching the subject 600. The infrared light scattered in this way may penetrate the at least one lens 620 and be delivered to the optical surface 630. In the case that the filter or film included in the optical surface 630 reflects infrared light and absorbs light other than infrared light, the optical surface 630 may selectively reflect only infrared light among a plurality of light rays delivered to the optical surface 630. The optical surface 630 including the filter or film reflecting infrared light may reflect an image associated with the subject 600 to which infrared light is irradiated, and may not reflect light other than infrared light, such as visible light, etc., emitted from the optical surface 630. The optical surface 630 according to an embodiment may include a filter or a film of a transparent material or a semi-transparent material (e.g., a hot mirror) capable of selectively reflecting infrared light or forming an image based on infrared light.

The camera 640 of the electronic device 601 may capture an image based on at least one light reflected through the optical surface 630 and may include the camera module 291. According to an embodiment, the camera 640 may be configured to selectively capture an image based on light of a particular wavelength. For example, the camera 640 may include an infrared camera that capture an image composed of infrared light.

According to an embodiment, the infrared camera may include a filter capable of reflecting or absorbing visible light emitted from the optical surface 630 and thus may selectively obtain an image composed of the infrared light reflected from the optical surface 630. The camera 640 may capture an image corresponding to the eyes of the user of the electronic device 602 or a surrounding area of the eyes in which the image has been reflected from the optical surface 630 based on infrared light. When capturing the image using a high-pixel camera, the camera 640 may obtain precise information regarding the user's eyes such as wrinkles around the user's eyes, twitches of the eyes, etc.

According to an embodiment, a path of the light reflected from the optical surface 630 may be changed through the reflective mirror 670. The reflective mirror 670 may be included in the electronic device 601 or the electronic device 602. Those of ordinary skill in the art may easily understand that various optical structures may be designed to deliver the light reflected from the optical surface 630 to the camera 640 by using at least one reflective mirror 670.

The processor 650 or 651 may be included in the electronic device 601 or 602 to control an operation or configuration of at least one of the light source 610, the at least one lens 620, the optical surface 630, the camera 640, the display 660, and the reflective mirror 670. For example, when irradiating infrared light toward the eyes of the user wearing the electronic device 602, the processor 650 or 651 may control the light source 610 to adjust the intensity of infrared light, a time during which the infrared light is irradiated, etc. In addition, the processor 650 or 651 may adjust a position of the at least one lens 620 to control a refractive index, etc. In addition, the processor 650 or 651 may also control an image or video displayed through the optical surface 630. The processor 650 or 651 may control the camera 640 to obtain at least one image reflected from the optical surface 630. In addition, the processor 650 or 651 may display at least one image, etc., obtained through the camera 640, by using the display 660 provided on an outer side of the electronic device 602. In addition, the processor 650 or 651 may control a position or an angle of the reflective mirror 670 to efficiently deliver the light reflected from the optical surface 630 to the camera 640.

The display 660 may be provided on the outer side of the electronic device 602. For example, the display 660 may be provided on a surface that opposes the surface on which the user wears the electronic device 602 (e.g., the surface on which the shielding portion 430 is positioned) to provide an image to another person facing the user wearing the electronic device 602.

The structure of the electronic device 601 or 602 disclosed in FIG. 6 is merely an example of the electronic device that may be designed variously, and the structure of the electronic device 601 or the structure of the electronic device 602 may be interchanged or shared with each other.

Figure 7:
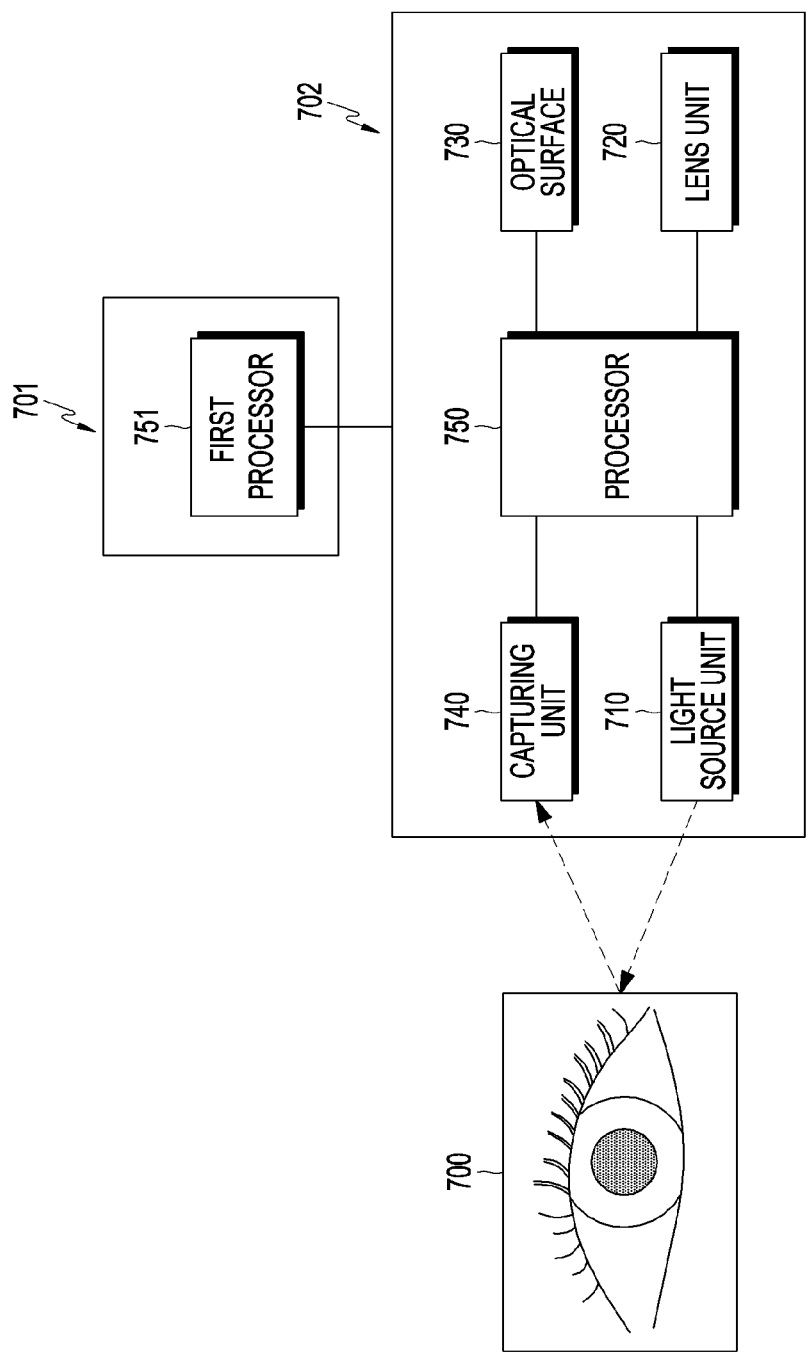
FIG. 7 is a block diagram of a structure of an electronic device according to various embodiments of the present disclosure.

FIG. 7 is a block diagram of a structure of an electronic device according to various embodiments of the present disclosure.

An electronic device 702 may be an HMD or a VR device. The electronic device 702 may include a light source unit 710 that irradiates light including a plurality of wavelengths to a subject 700, at least one lens unit 720 that refracts scattered light discharged from the subject 700, an optical surface 730 that reflects an image corresponding to the refracted scattered light, a capturing unit 740 that captures the image reflected from the optical surface 730, and a processor 750 that controls at least one of the light source unit 710, the lens unit 720, the optical surface 730, and the capturing unit 740 based on the image captured by the capturing unit 740.

For example, the processor 750 may irradiate infrared light to an iris of a user wearing the electronic device 702 through the light source unit 710. The infrared light irradiated to the iris may be scattered after reaching the iris. The processor 750 may adjust the position of the lens by controlling the lens unit 720 to deliver the infrared light scattered from the iris to the optical surface 730. The optical surface 730 may include a filter or a film capable of reflecting the received infrared light and allowing visible light discharged from the optical surface 730 to penetrate. To obtain a virtual image based on the infrared light reflected from the optical surface 730, the processor 750 may control the capturing unit 740 to capture the virtual image. In this case, the virtual image captured by the capturing unit 740 may include information corresponding to the user's iris. The processor 750 may recognize the user's iris based on the obtained virtual image and authenticate the user by using the recognized iris.

According to an embodiment, an operation of the processor 750 included in the electronic device 702 may be performed by a first processor 751 included in the electronic device 701 that may be separated from the electronic device 702 and may operate independently of the electronic device 702.

Figure 8A:
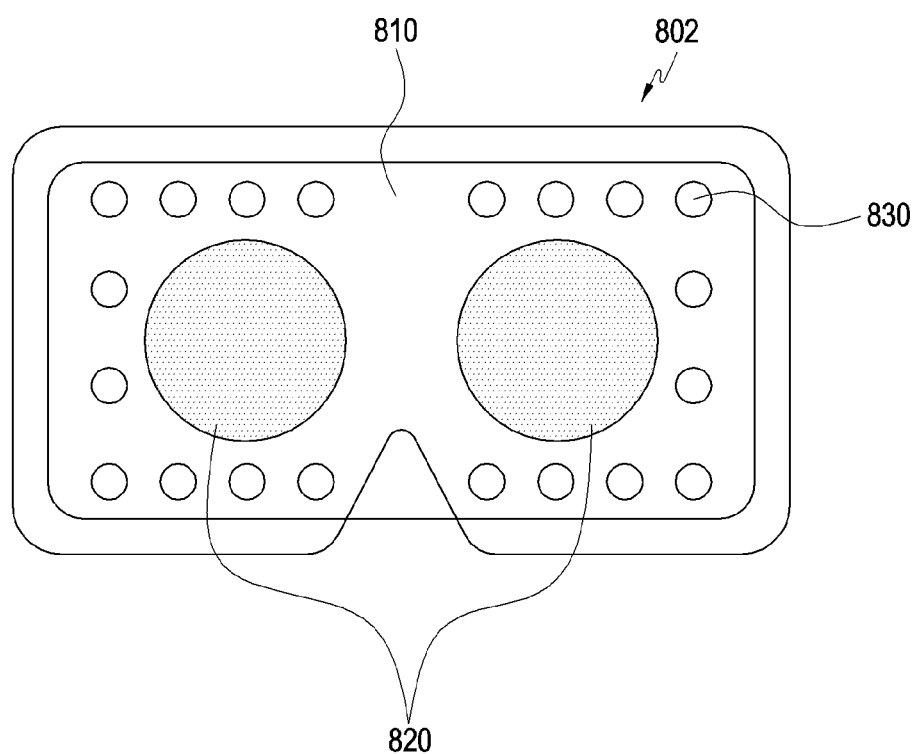
FIGS. 8A to 8C are views for describing a method of measuring a distance between an electronic device and a subject according to various embodiments of the present disclosure.
Figure 8B:
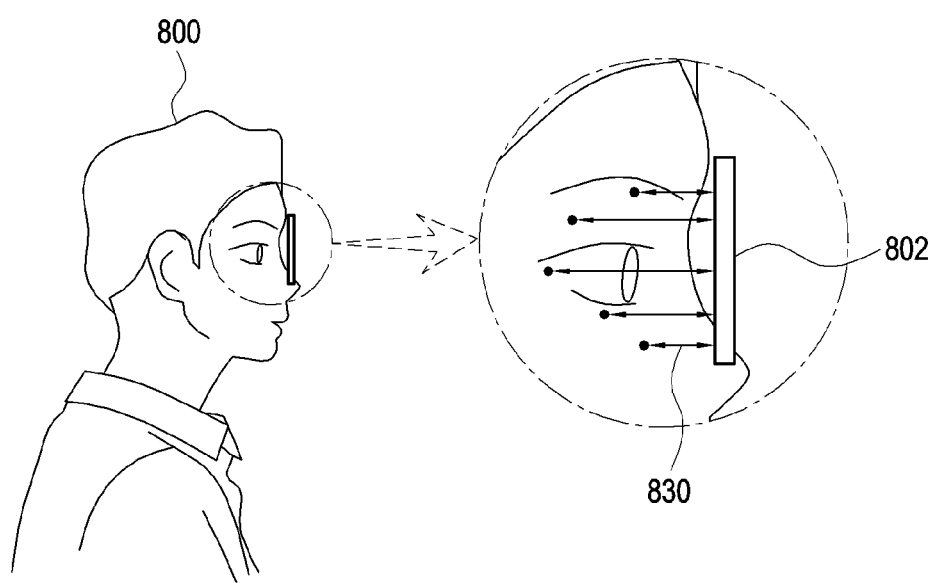
Figure 8C:
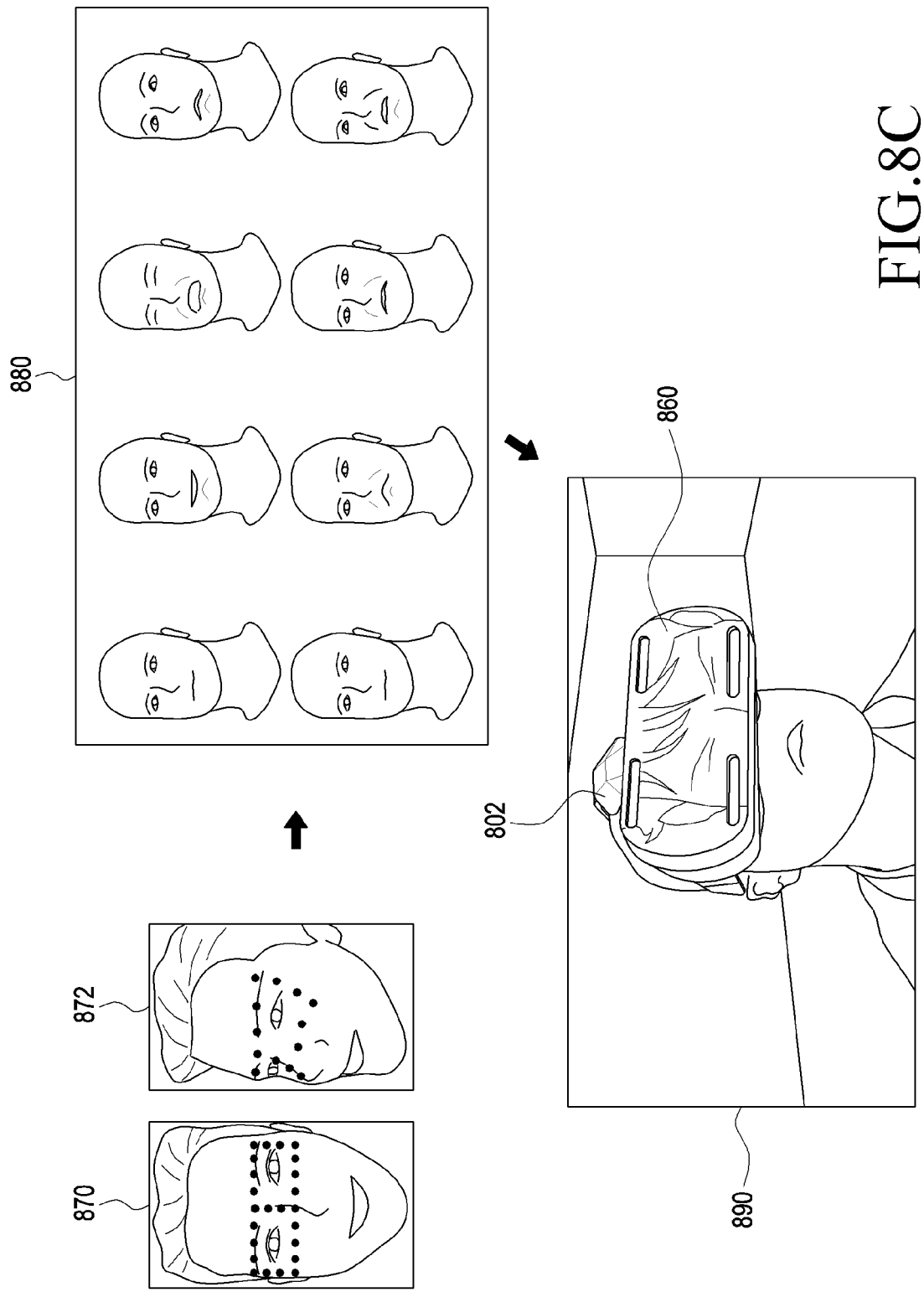

FIGS. 8A to 8C are views for describing a method of measuring a distance between an electronic device and a subject according to various embodiments of the present disclosure.

FIG. 8A is a rear view illustrating an electronic device according to various embodiments of the present disclosure, and FIG. 8B is a side view of a user wearing an electronic device according to various embodiments of the present disclosure.

An electronic device 802 may be an HMD or a VR device. The electronic device 802 may include a shielding portion 810 provided in a region corresponding to positions of the eyes of the user and an optical unit 820 that provides visual contents to the user wearing the electronic device 802.

The shielding portion 810 may be provided to surround the both eyes of the user wearing the electronic device 802 and may include at least one sensor 830 in an inside of the shielding portion 810. The at least one sensor 830 may include the sensor module 240. For example, the at least one sensor 830 may include a proximity sensor (e.g., 240G) capable of measuring a distance between the electronic device 802 and the user wearing the electronic device 802. In the case that the user has worn the electronic device 802, the processor may detect a motion in the user's eyes or the surrounding area of the eyes by using the proximity sensor provided in the inside of the shielding portion 810. More specifically, in the case that there is a motion in the eyes of the user wearing the electronic device 802 or the surrounding area of the eyes, the proximity sensor may detect a change in the distance between the fixed inside of the shielding portion 810 and the user's eyes or the surrounding area of the eyes. The processor may detect the blink of the eyes of the user, frowning of the eyes, twitches of the eyes or a motion in the wrinkle near the eyes, etc.

FIG. 8C is a view for describing a method of detecting a motion in the eyes of the user or the surrounding area of the eyes through the electronic device 802.

870 and 872 show the user's eyes or the surrounding area of the eyes that may be detected by a plurality of sensors in the case that the user wears the electronic device 802 including the plurality of sensors in the inside of the shielding portion 810. For example, a processor of the electronic device 802 may detect a motion of the eyes of the user wearing the electronic device 802 or the surrounding area of the eyes by using a plurality of proximity sensors. When the user wearing the electronic device 802 blinks or twitches the eyes, muscles near the eyes may move or wrinkles may appear in the surrounding area of the eyes and the proximity sensor of the electronic device 802 may detect a distance change corresponding to such a motion in the muscles or the wrinkles.

According to an embodiment, the processor may identify a facial expression of the user wearing the electronic device 802 based on the detected distance change and even predict the emotion of the user. The processor may identify the user's facial expression or emotion corresponding to the detected distance change by using data regarding the user's facial expression or emotion stored in advance in the memory.

As shown in 880, the data regarding the user's facial expression or emotion data may be stored in advance in the memory of the electronic device 802 or an external database. The processor may receive the data from the external database through a communication unit (e.g., the communication module 220) included in the electronic device 802 and identify the user's facial expression or emotion by using the received data.

As shown in 890, when identifying the user's facial expression or emotion corresponding to the detected distance change, the processor may display a virtual image corresponding to the user's facial expression or emotion through the display 860 included in the electronic device 802.

According to an embodiment, the processor may transmit the data regarding the identified user's facial expression or emotion to another electronic device which may deliver information corresponding to the received data to a user of the other electronic device. For example, when a first user wearing a first HMD and a second user wearing a second HMD communicate with each other, the first HMD may transmit information corresponding to an identified facial expression or emotion of the first user to the second HMD which may then provide contents corresponding to the facial expression or emotion of the first user to the second user based on the received information.

Figure 9:
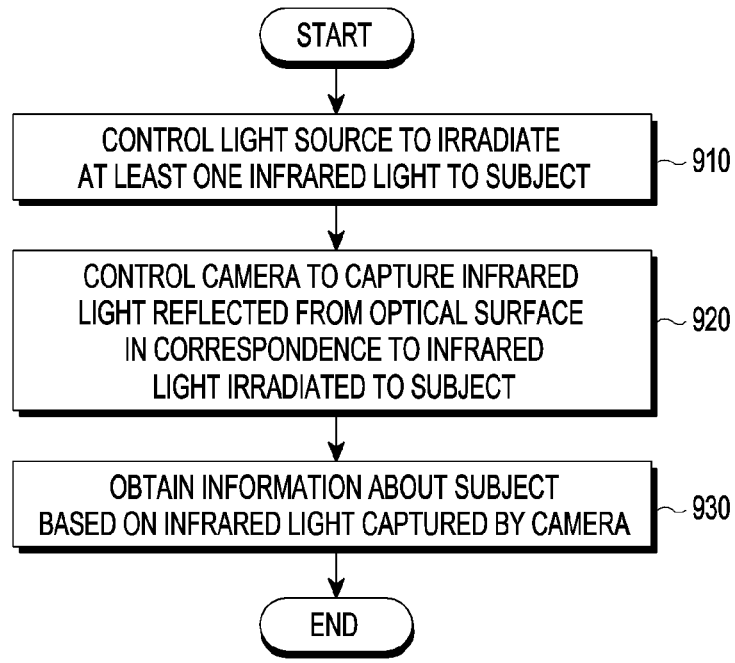
FIG. 9 is a flowchart of a control method of an electronic device according to various embodiments of the present disclosure.

FIG. 9 is a flowchart of a control method of an electronic device according to various embodiments of the present disclosure.

According to an embodiment, an electronic device including a light source that irradiates light including a plurality of wavelengths to a subject, at least one lens that refracts scattered light discharged from the subject, an optical surface that reflects an image corresponding to the refracted scattered light, a camera that captures an image reflected from the optical surface, and at least one processor may obtain information about the subject by using a method described below.

In operation 910, the processor may control the light source to irradiate at least one infrared light to the subject. According to an embodiment, the light source, which is an infrared light source capable of discharging infrared light, may irradiate infrared light to the eyes of the user wearing the electronic device and a surrounding area of the eyes. For example, when the user wears the electronic device, the eyes of the user may be positioned in the inside (e.g., the shielding portion 430) of the electronic device. At least one light irradiated from the light source located in the inside of the electronic device may be scattered after reaching the eyes of the user and the surrounding area of the eyes.

In operation 920, the processor may control the camera to capture infrared light reflected from the optical surface in correspondence to the infrared light irradiated to the subject. According to an embodiment, the optical surface may reflect light scattered from the body part of the user wearing the electronic device or form an image corresponding to the body part of the user. The optical surface may include a filter or a film that reflects the light delivered from the subject or forms an image corresponding to the subject. For example, the infrared light irradiated from the light source may be scattered after reaching the subject. The infrared light scattered in this way may penetrate the at least one lens and be delivered to the optical surface. In the case that the filter or film included in the optical surface reflects infrared light and absorbs light other than infrared light, the optical surface may selectively reflect only infrared light among a plurality of light rays delivered to the optical surface. The optical surface including the filter or film reflecting infrared light may reflect an image associated with the subject to which infrared light is irradiated, and may not reflect light other than infrared light, such as visible light, etc., emitted from the optical surface. The optical surface according to an embodiment may include a filter or a film of a transparent material or a semi-transparent material (e.g., a hot mirror) capable of selectively reflecting infrared light or forming an image based on infrared light.

According to an embodiment, the infrared camera may include a filter capable of reflecting or absorbing visible light emitted from the optical surface and thus may selectively obtain an image composed of the infrared light reflected from the optical surface. The camera may capture an image corresponding to the eyes of the user of the electronic device or a surrounding area of the eyes in which the image has been reflected from the optical surface based on infrared light. When capturing the image using a high-pixel camera, the camera may obtain precise information regarding the user's eyes such as wrinkles around the user's eyes, or twitches of the eyes, etc.

In operation 930, the processor may obtain information about the subject based on the infrared light captured by the camera. For example, to obtain a virtual image based on the infrared light reflected from the optical surface, the processor may control the camera to capture the virtual image. In this case, the virtual image captured by the camera may include information corresponding to the user's iris. The processor may recognize the user's iris based on the obtained virtual image and authenticate the user by using the recognized iris.

Figure 10:
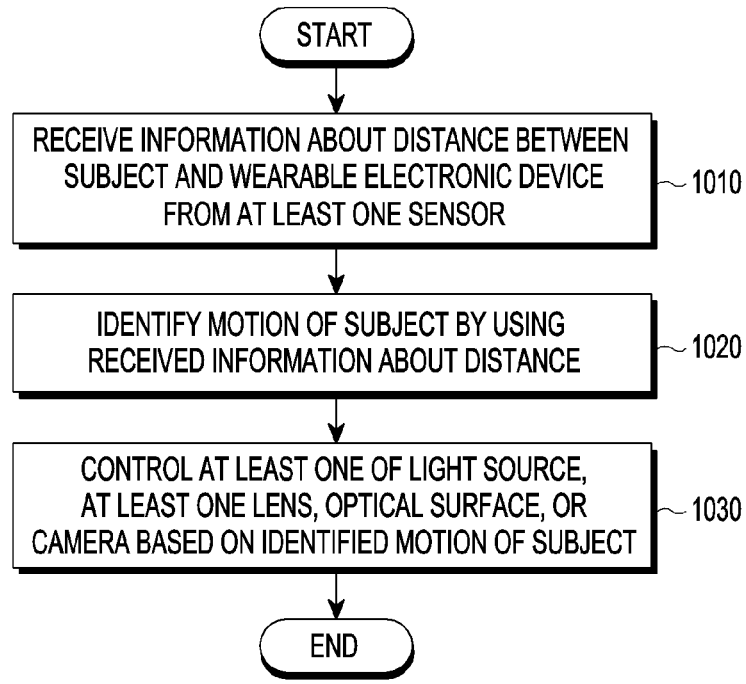
FIG. 10 is a flowchart of a control method of an electronic device according to various embodiments of the present disclosure.

FIG. 10 is a flowchart of a control method of an electronic device according to various embodiments of the present disclosure.

According to an embodiment, an electronic device including a light source that irradiates light including a plurality of wavelengths to a subject, at least one lens that refracts scattered light discharged from the subject, an optical surface that reflects an image corresponding to the refracted scattered light, a camera that captures an image reflected from the optical surface, at least one sensor that detects a distance, and at least one processor may obtain information about the subject by using a method described below.

In operation 1010, the processor may receive information about a distance between the subject and the electronic device from the at least one sensor. For example, the processor may periodically or aperiodically receive information about a distance between the eyes of the user wearing the electronic device or the surrounding area of the eyes and the inside of the shielding portion of the electronic device by using the at least one proximity sensor included in the electronic device.

In operation 1020, the processor may identify a motion of the subject by using the received information about the distance. For example, by periodically measuring the distance between the eyes of the user wearing the electronic device or the surrounding area of the eyes and the inside of the shielding portion of the electronic device, the processor may identify the motion in the eyes of the user or the surrounding area of the eyes.

In operation 1030, the processor may control at least one of elements included in the electronic device based on the identified motion of the subject. For example, the processor may control at least one of the light source, the at least one lens, the optical surface, and the camera based on the identified motion of the subject. Alternatively, the processor may identify the user's facial expression or emotion based on the identified motion in the eyes of the user or the surrounding area of the eyes. The processor may display a virtual image corresponding to the identified facial expression or emotion through the display included in the electronic device.

A method of obtaining information by capturing an eye according to various embodiments of the present disclosure includes identifying an image corresponding to light received by a camera, by using a wearable electronic device including a light source, at least one lens, an optical surface positioned on a first side of the at least one lens, and the camera configured to receive light, which is output from the light source and scattered by a subject located on a second side of the at least one lens, through the at least one lens and the optical surface, and controlling at least one of the light source, the at least one lens, the optical surface, and the camera, based on the identified image.

A method of obtaining information by capturing an eye according to various embodiments of the present disclosure includes controlling a light source to irradiate at least one infrared light to a subject, by using a wearable electronic device including the light source, at least one lens, an optical surface positioned on a first side of the at least one lens, and the camera configured to receive light, which is output from the light source and scattered by the subject located on a second side of the at least one lens, through the at least one lens and the optical surface, controlling the camera to receive at least one infrared light reflected from the optical surface in correspondence to the at least one infrared light irradiated to the subject, and obtaining information about the subject based on the at least one infrared light received by the camera.

A method of obtaining information by capturing an eye according to various embodiments of the present disclosure includes periodically receiving information about a distance between a subject and an wearable electronic device from at least one sensor by using the wearable electronic device including a light source, the at least one lens, an optical surface positioned on a first side of the at least one lens, and the camera configured to receive light, which is output from the light source and scattered by the subject located on a second side of the at least one lens, through the at least one lens and the optical surface, identifying a motion of the subject by using the received information about the distance, and obtaining information about the subject based on the identified motion of the subject.

A method of obtaining information by capturing an eye according to various embodiments of the present disclosure includes displaying an image corresponding to light received by a camera on at least one display by using a wearable electronic device including a light source, at least one lens, an optical surface positioned on a first side of the at least one lens, and the camera configured to receive light, which is output from the light source and scattered by a subject located on a second side of the at least one lens, through the at least one lens and the optical surface.

The present disclosure may include a recording medium readable by a computer on which a program for executing any one method disclosed herein is recorded.

Each of the foregoing elements described herein may be configured with one or more components, names of which may vary with a type of the electronic device. In various embodiments, the electronic device may include at least one of the foregoing elements, some of which may be omitted or to which other elements may be added. In addition, some of the elements of the electronic device according to various embodiments may be integrated into one entity to perform functions of the corresponding elements in the same manner as before they are integrated.

A term "module" used herein may comprise a unit configured to hardware, software, or firmware, for example, may be used interchangeably with terms such as logic, a logic block, a part, or a circuit. The "module" may be a part configured integrally, a minimum unit or a portion thereof performing one or more functions. The "module" may be implemented mechanically or electronically, and may include an application-specific integrated circuit (ASIC) chip, field-programmable gate arrays (FPGAs), and a programmable-logic device performing certain operations already known or to be developed.

At least a part of an apparatus (e.g., modules or functions thereof) or a method (e.g., operations) according to various embodiments may be implemented with an instruction stored in a computer-readable storage medium (e.g., the memory 130) in the form of a programming module. When the instructions are executed by a processor (for example, the processor 120), the processor may perform functions corresponding to the instructions.

The computer-readable recording medium includes hard disk, floppy disk, or magnetic media (e.g., a magnetic tape, optical media (e.g., compact disc read only memory (CD-ROM) or digital versatile disc (DVD), magneto-optical media (e.g., floptical disk), an embedded memory, and so forth. The instructions may include a code generated by a compiler or a code executable by an interpreter. Modules or programming modules according to various embodiments of the present disclosure may include one or more of the foregoing elements, have some of the foregoing elements omitted, or further include additional other elements. Operations performed by the module, the program, or another component according to various embodiments may be carried out sequentially, in parallel, repeatedly, or heuristically, or one or more of the operations may be executed in a different order or omitted, or one or more other operations may be added.

The embodiments disclosed herein have been provided for description and understanding of disclosed technical matters, and are not intended to limit the scope of the present disclosure. Therefore, it should be construed that the scope of the present disclosure includes any change or other various embodiments based on the technical spirit of the present disclosure.

The invention claimed is:

1. A wearable electronic device comprising:
at least one lens;
an optical surface positioned on a first side of the at least one lens;
a display positioned on the optical surface;
a light source configured to output light toward a subject located at a second side of the at least one lens, wherein the subject includes eyes and a surrounding area of the eyes of a user wearing the wearable electronic device;
a camera configured to receive the light, which is output from the light source and scattered by the subject located on the second side of the at least one lens, through the at least one lens and the optical surface;
at least one sensor configured to detect a distance between the subject and the wearable electronic device from a fixed inside portion of the wearable electronic device;
a memory to store data related to at least one of a facial expression or an emotion; and
at least one processor configured to:
obtain, based on, at least in part, the light received by the camera, first information about the subject including a first distance from the fixed inside portion to the subject detected by the at least one sensor,
identify a change in the first distance based on a second distance previously detected by the at least one sensor,
obtain a first data related to at least one of a facial expression or an emotion stored in the memory,
obtain second information including a second data related to at least one of a facial expression or an emotion corresponding to the change in the first distance, wherein the second data identified based on the first data, and
control the display to display a virtual image obtained based on the second information.

2. The wearable electronic device of claim 1, wherein the at least one processor is further configured to:
identify an image corresponding to the light received by the camera; and
control at least one of the light source, the at least one lens, the optical surface, or the camera, based on the identified image.

3. The wearable electronic device of claim 2, wherein the at least one processor is further configured to:
control the light source to irradiate infrared light to the subject;
control the camera to receive the infrared light reflected from the optical surface in correspondence to the infrared light irradiated to the subject; and
obtain the first information about the subject based on, at least in part, the infrared light received by the camera.

4. The wearable electronic device of claim 2,
wherein the at least one processor is further configured to:
periodically receive the first information including the first distance from the at least one sensor;
identify a motion of the subject by using the received first information; and
identify the change in the first distance about the subject based on the identified motion of the subject.

5. The wearable electronic device of claim 1, further comprising an input/output interface configured to electrically connect the wearable electronic device to a processor provided in a mobile electronic device attachable to or detachable from the wearable electronic device,
wherein the processor is configured to:

identify an image corresponding to the light received by the camera; and control at least one of the light source, the at least one lens, the optical surface, or the camera, based on the identified image.

6. The wearable electronic device of claim 1, further comprising at least one display on an outer side of the wearable electronic device, wherein the at least one processor is further configured to control the at least one display to display an image corresponding to the light received by the camera.

7. The wearable electronic device of claim 1, wherein the light source is positioned between the subject and the at least one lens.

8. The wearable electronic device of claim 1, wherein the light source is positioned between the optical surface and the at least one lens.

9. The wearable electronic device of claim 1, wherein the at least one lens is positioned between the subject and the optical surface and comprises a convex lens.

10. The wearable electronic device of claim 1, wherein the subject comprises an eye of a user wearing the wearable electronic device, and wherein the camera is further configured to obtain an image of the subject based on the first information.

11. The wearable electronic device of claim 1, further comprising a display positioned on the first side, wherein the optical surface is positioned on the display.

12. The wearable electronic device of claim 1, wherein the optical surface is positioned on a display provided in a mobile electronic device attachable to or detachable from the wearable electronic device.

13. The wearable electronic device of claim 1, wherein the optical surface comprises a filter configured to penetrate visible light and reflect infrared light.

14. The wearable electronic device of claim 1, wherein the camera comprises an infrared camera configured to capture infrared light among light rays reflected from the optical surface.

15. The wearable electronic device of claim 1, further comprising:

a communication interface configured to communicate with a second wearable electronic device, wherein the at least one processor is further configured to transmit the second information to the second wearable electronic device for display on the second wearable electronic device.

16. A method of obtaining information by capturing an eye, the method comprising:

obtaining first information about a subject based on, at least in part, light received by a camera, by using a wearable electronic device including:

at least one lens, an optical surface positioned on a first side of the at least one lens, a light source configured to output light towards the subject located on a second side of the at least one lens and the camera configured to receive the light, which is output from the light source and scattered by the subject located on the second side of the at least one lens, through the at least one lens and the optical surface, at least one sensor configured to detect a first distance between the subject and the wearable electronic device from a fixed inside portion of the wearable electronic device, and a memory to store a first data related to at least one of a facial expression or an emotion data;

identifying a change in the first distance based on a second distance previously detected by the at least one sensor;

obtaining second information including a second data related to at least one of a facial expression or an emotion corresponding to the change in the distance, wherein the second data is identified based on the first data obtained from the memory; and displaying a virtual image obtained based on the second information on a display of the wearable electronic device, wherein the subject includes eyes and a surrounding area of the eyes of a user wearing the wearable electronic device.

17. The method of claim 16, further comprising:

identifying an image corresponding to the light received by the camera; and controlling at least one of the light source, the at least one lens, the optical surface or the camera, based on the identified image.

* * * * *